(12) United States Patent
Zadyraka et al.

(10) Patent No.: US 9,034,194 B2
(45) Date of Patent: May 19, 2015

(54) APPARATUS FOR TREATING A FLUID WITH MICROWAVE RADIATION

(75) Inventors: Yuriy Vladimirovich Zadyraka, Edinburgh (GB); Sergey Ivanovich Gritsinin, Moscow (RU); Mamikon Aramovich Misakyan, Klin (RU); Igor Antonovich Kossyi, Moscow (RU); Eduard Mikailovich Barkhudarou, Moscow (RU)

(73) Assignee: ADVANCED MICROWAVE TECHNOLOGIES LTD, Edinburgh (GB)

( * ) Notice: Subject to any disclaimer, the term of this patent is extended or adjusted under 35 U.S.C. 154(b) by 235 days.

(21) Appl. No.: 13/503,003

(22) PCT Filed: Oct. 23, 2009

(86) PCT No.: PCT/GB2009/002549
§ 371 (c)(1),
(2), (4) Date: Aug. 7, 2012

(87) PCT Pub. No.: WO2011/048349
PCT Pub. Date: Apr. 28, 2011

(65) Prior Publication Data
US 2012/0305496 A1    Dec. 6, 2012

(51) Int. Cl.
*B01J 19/12*    (2006.01)
*G21K 5/02*    (2006.01)
(Continued)

(52) U.S. Cl.
CPC ............ *B01J 19/126* (2013.01); *A23L 3/01* (2013.01); *A23L 3/22* (2013.01); *A61L 2/0064* (2013.01);
(Continued)

(58) Field of Classification Search
USPC ......... 219/600, 678, 681, 685, 688, 690, 702, 219/704, 710; 210/198.1, 243, 153, 143, 210/748.01, 748.07; 422/21, 105, 243, 186
See application file for complete search history.

(56) References Cited

U.S. PATENT DOCUMENTS 5,014,010 A * 5/1991 Helms et al. .................. 324/640
5,400,524 A    3/1995 Leconte et al.
(Continued)

FOREIGN PATENT DOCUMENTS

| DE | 19606517 A1 | 8/1997 |
|---|---|---|
| JP | 2004-172044 | 6/2004 |
| JP | 2008-302281 | 12/2008 |
| WO | WO2004/010454 A2 | 1/2004 |
| WO | WO 2008017137 A1 * | 2/2008 |

OTHER PUBLICATIONS

International Search Report for PCT/GB2009/002549 dated Jul. 21, 2010.
(Continued)

*Primary Examiner* — Walter D Griffin
*Assistant Examiner* — Cameron J Allen
(74) *Attorney, Agent, or Firm* — Moore & Van Allen PLLC; W. Kevin Ransom

(57) ABSTRACT

An apparatus for treating a flow of fluid with microwave radiation, the apparatus comprising: a vessel having a sidewall and opposed first and second end walls defining a substantially cylindrical chamber, the first end wall being disposed a predetermined distance $d_1$ from the second end wall; a pipeline for flowing fluid through, the pipeline passing through the first end wall towards the second end wall of the vessel, the chamber and the pipeline being substantially coaxial and the pipeline being substantially transparent to microwave radiation; and a microwave radiation inlet in the side wall of the vessel for admitting microwave radiation of wavelength λ into the chamber, wherein the distance $d_1$ is substantially equal to an integral multiple of $\lambda/2$ so that the chamber is a microwave resonator.

25 Claims, 3 Drawing Sheets

(51) Int. Cl.
  *A23L 3/01*   (2006.01)
  *A23L 3/22*   (2006.01)
  *A61L 2/00*   (2006.01)
  *A61L 2/12*   (2006.01)
  *A61L 2/24*   (2006.01)
  *H05B 6/80*   (2006.01)

(52) U.S. Cl.
  CPC ... *A61L 2/12* (2013.01); *A61L 2/24* (2013.01); *A61L 2202/22* (2013.01); *B01J 2219/1227* (2013.01); *B01J 2219/1242* (2013.01); *B01J 2219/1269* (2013.01); *B01J 2219/1272* (2013.01); *B01J 2219/129* (2013.01); *H05B 6/802* (2013.01)

(56) References Cited

U.S. PATENT DOCUMENTS

| | | | |
|---|---|---|---|
| 5,834,744 A | 11/1998 | Risman | |
| 5,869,817 A * | 2/1999 | Zietlow et al. | 219/696 |
| 7,034,266 B1 * | 4/2006 | DeGroot et al. | 219/700 |
| 2006/0163054 A1 | 7/2006 | Spitzl et al. | |

OTHER PUBLICATIONS

International Preliminary Report on Patentability for PCT/GB2009/002549 dated Apr. 24, 2012.

Japanese Office Action; Notification of Reason(s) for Refusal; Dispatch No. 565270, Aug. 28, 2013.

* cited by examiner

APPARATUS FOR TREATING A FLUID WITH MICROWAVE RADIATION

FIELD OF THE INVENTION

The present invention relates to a microwave apparatus and method for treating fluids, slurries, semi solids and suspensions. The treatment includes, for example, heating, melting, sterilisation, pasteurisation, cooking, stimulating chemical reactions and fractionation.

BACKGROUND OF THE INVENTION

Apparatus and methods for treating, sterilising and pasteurising fluids using microwave radiation are known. Typically, these involve complex components that are difficult and expensive to manufacture and construct, frequently necessitating waveguides and high power sources of radiation energy, as exemplified in RU2087084.

SUMMARY OF THE INVENTION

According to one aspect of the present invention, there is provided an apparatus for treating a flow of fluid with microwave radiation, the apparatus comprising: a vessel having a sidewall and opposed first and second end walls defining a substantially cylindrical chamber, the first end wall being disposed a predetermined distance $d_1$ from the second end wall; a pipeline for flowing fluid through, the pipeline passing through the first end wall towards the second end wall of the vessel, the chamber and the pipeline being substantially coaxial and the pipeline being substantially transparent to microwave radiation; and a microwave radiation inlet in the side wall of the vessel for admitting microwave radiation of wavelength $\lambda$ into the chamber, wherein the distance $d_1$ is substantially equal to an integral multiple of $\lambda/2$ so that the chamber is a microwave resonator.

The apparatus of the present invention provides a highly efficient means of transferring microwave radiation energy from a microwave radiation source to the fluid to be treated.

The terms treatment, treat, treated with microwave radiation and associated forms thereof can include thermal treatment, non-thermal treatment and include any of cooking, pasteurisation, sterilisation, coagulation, fractionating and partial or substantially complete inactivation or destruction of bio-molecules and/or other molecular species like viruses and/or protozoa.

The microwave radiation treatments of the invention are particularly effective in relation to proteinaceous fluids, such as for example blood and milk. The treatment can result in the fractionation or destruction of certain components of the proteinaceous fluid.

For a given microwave radiation source, typically a magnetron, having a given operating frequency, the wavelength ($\lambda$) of the microwave radiation obtained, will to some extent depend upon the parameters of the resonator chamber and its contents. Thus, for example, whilst a 2.45 GHz magnetron would provide microwave radiation with $\lambda$=12.2 cms in a vacuum, typically in the chamber of an apparatus of the invention there is obtained microwave radiation with $\lambda$=of the order of 13.0 cms.

The efficiency of the microwave resonator provided by the vessel chamber is sensitive to the distance $d_1$ between the opposed end walls of the vessel, the degree of sensitivity depending on the multiple of $\lambda/2$ to which $d_1$ corresponds. Efficiency is very highly sensitive to deviations of $d_1$ by as little as ±1% from $\lambda/2$, but is significantly less sensitive to deviations of $d_1$ by as much as ±10% from $\lambda$ (=2×$\lambda/2$). Furthermore the efficiency reduces with increasing multiples of $\lambda/2$. The greater the number of multiples of $\lambda$ the more cumbersome the apparatus becomes. Desirably therefore $d_1$ is from 1 to 3 times $\lambda/2$, advantageously 1 or 2 times $\lambda/2$. Most preferably $d_1$ is substantially equal to $\lambda$ (=2×$\lambda/2$).

The internal diameter $d_2$ of the vessel chamber is less critical than the length $d_1$. It is, however, desirable for said diameter $d_2$ to be chosen so as to be not greater than $2\lambda$ and not less than $0.6\lambda$. Desirably $d_2$, is from 1 to $2\lambda$.

The vessel chamber walls should normally be of or be coated with an electrically conducting material, desirably a metal with high electrical conductivity, preferably stainless steel, copper, aluminium, brass etc. Conveniently, the chamber walls are silver plated or gold plated. The material is generally chosen so as to minimise leakage of microwave radiation from the interior of said vessel chamber, or absorption of the microwave radiation by the vessel chamber walls.

Any convenient source of microwave radiation may be used with the present invention. A standard commercially available magnetron such as that used in microwave cooking apparatus may be used. These are widely available, relatively cheap and can be easily incorporated into an apparatus according to the present invention. Such magnetrons typically generate microwaves with a frequency in the range from 2.3 to 2.7 GHz, for example about 2.45 GHz or 2.6 GHz (corresponding to wavelengths ($\lambda$) which typically provide microwave radiation in the chamber, of from 13.04 to 11.11 cms, e.g. about 12.24 or 11.54 cms).

The microwave radiation is introduced into the vessel chamber via a microwave radiation inlet through the sidewall of said vessel chamber. Preferably the microwave radiation inlet is off-centre with respect to the longitudinal extent of the chamber ($d_1$) being desirably at a position at which the microwave energy level along the central longitudinal axis is from 30 to 60%, advantageously from 40 to 50%, of the maximum energy level. The actual position between the end walls will of course depend on the relation between $d_1$ and $\lambda$. Where $d_1 \approx \lambda$, then a suitable position could in principle be at any of 10 to 15%, 30 to 35%, 55 to 60%, or 75 to 80% of $d_1$ from the upstream end wall to the downstream end wall. Most preferably, though, the microwave radiation inlet is at 75 to 80% of $d_1$.

Locating the microwave radiation inlet closer to the second (downstream) end wall, towards which the fluid flows, provides more gradual treatment and heating to the fluid flowing through the pipeline to be treated as the fluid will be partially treated prior to reaching the point along the pipeline where maximum microwave energy is supplied.

When a fluid is present in the pipeline it is not generally necessary to provide protection for the microwave radiation source, which helps to significantly reduce manufacturing cost and complexity of the apparatus. Nevertheless, if desired, protection against significant reflection of microwave energy back into the source, could be used, in which case other positions of the microwave radiation inlet could also be used without the risk of damage to the source. Suitable protection devices are generally well known in the art and typically comprise ferrite components configured to act as a microwave non-return valve on the waveguide extending from the magnetron.

Various different orientations of the apparatus could be used, including for example, apparatus with a horizontal pipeline alignment and apparatus with a vertical pipeline alignment. The latter is generally preferred as it substantially minimises the risk of gas bubbles being trapped inside the chamber, which could possibly result in damage to the microwave radiation source. Nevertheless other arrangements, e.g. with an inclined pipeline, may also be used. Where a horizontally aligned pipeline is used suitable bubble-trapping means may be provided, various examples of which are well known in the fluid handling art. For example, the downstream end of the pipeline can be in fluid communication with a pipe whose outlet is at a higher level than the apparatus. References to side and end walls of the chamber are relative to the arrangement of the pipeline within the chamber, irrespective of orientation of the apparatus.

A suitable magnetron microwave radiation source generally has a generally cylindrical rod antenna extending outwardly from the main body of the magnetron via which the microwave radiation is emitted. The vessel chamber is formed and arranged for coupling with the microwave radiation source so as to form a substantially microwave radiation leak proof connection. The body of the microwave radiation source may be set back from the chamber sidewall such that the antenna, which generally has a length $\simeq \lambda/4$, extends from the body of the microwave radiation source towards and into the vessel chamber. Performance of the apparatus is relatively sensitive to the position of the distal and proximal ends of the antenna relative to the chamber sidewall and pipeline.

The distal (free) end of the antenna may be disposed at a predetermined projecting distance $d_3$ from the chamber sidewall less than or equal to $\lambda/4$ and greater than or equal to $3\lambda/16$. As the $d_3:\lambda$ ratio departs from the preferred ratio there is an increased heat transfer to the magnetron due to reflection of microwaves back to itself which may result in damage to the magnetron. This undesirable energy transfers also results in less efficient treatment of the flowing fluid. Desirably $d_3$ is within +/−10% of $\lambda/5$.

The performance of the apparatus has also been found experimentally to be sensitive to the position of the antenna from the end walls of the chamber along the length of the chamber, $d_1$. These distances will be referred to as $d_4$ and $d_5$ where $d_4$ is the distance of the antenna from one of the end walls, $d_5$ is the distance of the antenna from the other end wall, $d_4$ and $d_5$ being equal to $d_1$.

In a preferred aspect the present invention provides a fluid treatment apparatus comprising a fluid handling apparatus of the invention provided with a microwave radiation source coupled to said microwave radiation inlet.

The apparatus may be provided with temperature sensing and monitoring means for sensing the temperature of the fluid being treated. Suitable temperature sensors include, but are not limited to resistance thermometers, thermocouples etc. Such a temperature sensor may be connected to a microwave radiation source control which can vary the intensity of microwave radiation provided, or, more conveniently, connected to a fluid flow controller such as a variable flow rate pump, a flow restriction valve, etc, in order to prevent overheating of the fluid. This is important where heat-sensitive fluids, such as biological fluids, blood, plasma, milk etc are being treated, and it is necessary to avoid overheating of the fluid, e.g. in order to prevent solidification or coagulation of fluid contents etc. Such fluid control is also important in certain applications to enable the precise control of temperatures and exposure times in situations where these parameters are critical, for example cooking, pasteurisation, sterilization, fractionation or controlling chemical reactions.

An advantage of the present invention is that the non-contact nature of the heating provided by the microwave radiation generally provides a significantly reduced risk of localised overheating of the fluid flow, particularly on the inner walls of the pipeline.

The pipeline is preferably of substantially microwave radiation-transparent material, which does not absorb microwave energy to any significant extent. Preferably such a material has a dielectric constant in the range from 2 to 4. Suitable materials include quartz, polyethylene, and preferably PTFE (polytetrafluorethene).

The pipeline wall may be of any convenient thickness, but should be sufficiently strong to withstand the pressure exerted by the fluid being pumped through the pipeline. In general, the pipeline has a wall thickness in the range from 3 to 10 mm, typically 5 to 8 mm. Such a pipeline could act as a dielectric antenna on its own permitting microwaves to propagate through the pipeline material until they are absorbed by fluid in the pipeline.

As the microwave radiation energy increases the temperature of fluid flowing through the pipeline, the dielectric constant of the fluid is decreased and microwave radiation penetration increases. As a result of this, fluid at the centre (i.e. along the central longitudinal axis) of the pipeline is subjected to more intensive treatment. Advantageously, there is provided a static or dynamic mixer device inside the pipeline to increase the uniformity of treatment of the fluid flow between the radially inner and radially outer zones of the pipeline.

To further increase the absorption of microwave radiation by the flowing fluid the apparatus may have a pre-heating device. Such a pre-heater can be of a variety of forms including fluid contact based electrical resistance heating elements, heat exchangers, etc. providing heat by means of conduction from a heat exchange fluid passed through a heat exchange element, other kinds of radiation based energy sources such as radiant energy or convection heaters. In general preheating is desirably carried out so as to bring the fluid temperature. This has the advantage of increasing penetration of the microwave energy into the fluid, thereby increasing the efficiency of the treatment process. Where a preheater is used, care should be taken to avoid localised overheating of the fluid, in order to avoid coagulation etc. For instance when blood is heated, a temperature 40 C should not be exceeded. The cooling medium used for cooling the magnetrons and possibly other components may be used as a source of heat for preheating the fluid.

A pump may be provided for driving the fluid to be heated through the pipeline. A variety of different pumps are suitable including, but not limited to gear pumps, reciprocating piston and cylinder type pumps, vane pumps, swash plate pumps, peristaltic pumps, and positive displacement devices when operated as pumps, progressive cavity pumps, etc.

The apparatus may be provided in a modular form with a plurality of individual apparatuses of the invention interconnected in series so that a fluid flow can be subjected to microwave irradiation from the respective microwave radiation sources of successive modules. This has the advantage of enabling longer treatment residence times for a given flow rate to be achieved, whilst maintaining high flow rates and/or optimum individual microwave treatment apparatus module configuration. In this connection, the down-stream and up-stream ends of the pipeline of successive modules may be interconnected so as to enable a substantially uninterrupted flow of fluid therethrough. As a further alternative a plurality of modules could be connected in parallel.

Preferably, the pipeline outer diameter $d_6$ is $\geq \lambda/\pi$. For example, when microwaves with $\lambda$ approximately equal to 13 cm are used $d_6$ is preferably in the range from 41 mm to 65 mm, most preferably from 45 mm to 50 mm in order to limit interaction of the microwave radiation sources of interconnected modules. By interconnecting the vessel chambers, the fluid flowing through the pipelines may be sequentially treated in the plurality of vessel chambers as it flows through the pipeline. By increasing the number of connected vessel chambers the flow rate of fluid can be increased thereby facilitating the treatment of larger fluid volumes. Spacers may be introduced between individual modules to increase the pipeline length for any given number of treatment modules. By varying the number of treatment modules the retention time of the fluid can be varied for any given temperature.

A pressure control system may be provided at the outlet of the device to allow the pressure in the device to be varied. This can help facilitate a range of treatment parameters that are limited by the physical properties of the pipeline materials and constructions.

When a number of vessel chambers are interconnected there is the possibility of microwaves penetrating into neighbouring vessel chambers. It has been found that where the preferred pipeline outer diameter $d_6$ is also less than $\lambda/2$ and the end walls of the chamber are in the form of a diaphragm around the pipeline the incidence of microwave penetration between the vessel chambers is reduced. Typically, the diaphragm is of a metal such as gold, copper or brass. Stainless steel could also be used as an alternative, though this would be less effective. Meshed metal would also be suitable. However, this is generally more expensive than sheet metal.

Preferably the thickness of the annular space between the inside of the vessel chamber and the outside of the pipeline ($d_7$) (i.e. $d_2$-$d_6$) is equal to $\lambda/2 \pm 1\%$.

The inner diameter of the pipeline $d_8$ is chosen to be of suitable dimension depending on the fluid that is to be treated and the penetration of microwaves therethrough. The greater the microwave penetration the greater $d_8$ can be while still providing effective treatment of fluid at the centre of the pipeline. For example it is known that microwaves can penetrate through approximately 10 to 12 mm of water, whereas in blood they can penetrate further, the penetration increasing as the temperature of the blood increases. The upper level of penetration for heated blood appears to be approximately 15 mm. Pipelines with an inner diameter $d_8$ of 30 mm to 32 mm have been found to be suitable in an apparatus for treating blood.

The inventors have found that values of the dimensions $d_1$ to $d_8$ of the components of the apparatus can typically be determined according to the following process. The inner diameter of the chamber $d_2$ is determined on the basis of readily available standard pipes which are of appropriate size to provide an apparatus of practical size and satisfy the preferred range of being not less than $0.6\lambda$ and not greater than $2\lambda$. A pipe is then chosen. This has to have an inner diameter $d_8$ suitable for the fluid to be treated, as described above, and an outer diameter that falls within the preferred range $\lambda/\pi \geq d_6 < \lambda/2$.

The value $d_1$ is generally predetermined according to the multiple of $\lambda/2$ chosen and the remaining dimensions $d_3$ and $d_4$ (and hence $d_5$) can be readily determined by experimentation. This is typically done by measuring the increase in temperature of the treated fluid and of the magnetron over a period of 1 minute for different, values of $d_3$ and $d_4$, the desired values being those which provide maximum fluid temperature and minimum magnetron temperature, increases. Such an arrangement provides the most efficient conditions for heating the fluid as the amount of microwave energy reflected back to the magnetron and hence not absorbed by the fluid is minimised.

In a further aspect the present invention provides a method of treating a fluid with microwave radiation comprising the steps of: providing a fluid treatment apparatus of the present invention; and passing a flow of said fluid through the pipeline of said apparatus whilst subjecting it to microwave radiation from the microwave radiation source of said apparatus.

The rate of fluid flow through the apparatus may be varied as required depending on various factors such as the pipeline capacity, acceptable fluid back pressure, treatment intensity required, retention times, treatment temperature microwave radiation energy supplied fluid supply temperature, fluid properties such as suspended solids content, dielectric constant, conductivity levels, microwave penetration, degree of mixing, etc. In general suitable flow rates can be readily determined by simple trial and error. Conveniently in at least some cases, a suitable flow rate can be obtained by simply adjusting the flow rate so as to achieve a predetermined temperature level at the downstream end of the apparatus (whether this is a single chamber apparatus or a multi-chamber modular apparatus). Thus, for example, for the purposes of sterilisation of a biological waste fluid such as blood, the flow rate is preferably controlled so as to achieve a fluid temperature of at least 98 C at atmospheric pressure.

A stirring device may be provided to stir the fluid as it flows through the apparatus. This reduces the likelihood of the pipeline becoming blocked due to a build up of residual or coagulated residue in the pipeline and facilitates maintenance of the apparatus by reducing the time required to clean the system. The stirring device reduces the occurrence of "hot spots" building up as the apparatus is operated. A particularly simple and convenient stirring device comprises an elongate rod, for example a 3 to 4 mm stainless steel rod, or a helical wire or metal rod which extends centrally along the length of the pipeline and is drivingly connected at one end to a rotary drive device, conveniently an electronic motor. Preferably the wire or rod should be covered and/or protected by PTFE tube of appropriate inner diameter.

In thick liquids like blood the stirring device is best mounted on one side of a hub so that the stirring devise is 0.5 mm distant from the wall of the pipeline. Several stirring devices can be arranged in pairs on opposite sides of the hub depending on the nature of the fluid. The speed of rotation is critical and dependent on the fluid being treated and the purpose of treatment. In the case of a high protein liquid, like blood, a speed of 2800 rpm is optimum. For other liquids and applications the optimum speed can be determined by trial and error.

The direction of the flow of the fluid over the rotation devise is important. Generally where the fluid is viscous, the flow rate is relatively high (17 liters/min) or there is a large amount of large suspended solids it is best to have the liquid flowing away from the rotation devise. This can be achieved by positioning the rotation unit at the down stream end of the treatment chamber. Where the flow is low (below 17 1/min) and the liquid is viscous with no large suspended solids it is best to have the fluid flowing towards the rotation unit. This can be achieved by having the rotation unit positioned at the upstream end of the treatment chambers.

In certain circumstances, particularly where the fluid is very viscous and the level of suspended solids is high, it is advantageous to change the direction of rotation at regular intervals to ensure there is no build up of solid material on the rotation devise. In the case of blood such an interval is ten minutes.

Depending on the type of fluid being treated and the treatment temperatures, it may be necessary to coat the stirring devise with a suitable material to avoid adhesion by the fluid or its constituents. Such suitable materials are, but not limited to, PTFE and PEEK. In such circumstances, inserting the stirring devise into a tube made from a suitable material may be best. Such a tube may have an internal diameter the same as the external diameter of the stirring devise. Where such a method is used, the hub connecting the stirring devise to the method of rotation should be constructed in two halves so that it can be used as a clamp to connect both the stirring devise and its cover to the rotation devises. In certain applications, where the speed of the stirring device is slow alternative materials can be used to advantage to substitute for the stainless steel rod or wire. Such materials should be substantially microwave radiation transparent and should not absorb microwave energy to any great extent. Preferably such a material has a dielectric constant in the range from 2-4. Such materials include but are not limited to, PTFE (Polytetrafluorethene) and PEEK (Polyetheretherketone). The diameter of rods made from these materials will generally be larger than their equivalents made from stainless steel.

A wide variety of fluids, emulsions, suspensions, semi solids and solids carried in a liquid may be treated by means of the present invention for various purposes. Thus many fluids used and processed in the food industry such as milk, blood, fruit juices, brewery products and fats may be sterilised, pasteurised, cooked or melted. Many solids capable of being carried in a fluid like rice, offal, mechanically recovered meat may be sterilised, pasteurised or cooked. Many high protein fluids particularly biological fluid materials such as body fluids, including one or more of blood, serum, lymph fluid, as well as food and beverage industry waste, may be fractionated by coagulation and/or sterilised so as to make them acceptable for discharge into the public sewer or any other simple means. Fluids containing several reactants can be treated to enhance reaction times and yields.

BRIEF DESCRIPTION OF THE DRAWINGS

Further preferred features and advantages of the invention will appear from the following examples and detailed description illustrated with reference to the accompanying drawings of which.

DETAILED DESCRIPTION OF THE DRAWINGS

Figure 1:
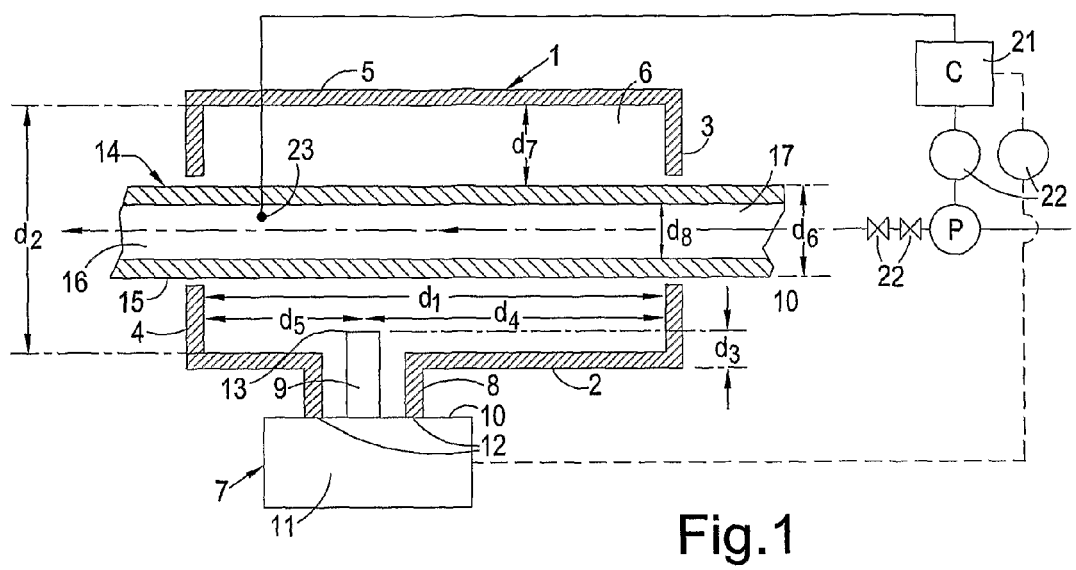
FIG. 1 is a schematic sectional view through a fluid treatment apparatus.

FIG. 1 shows a fluid treatment apparatus 1 comprising a vessel 2 with a first upstream end wall 3 and a second downstream end wall 4 opposed a distance $d_1$ apart, and a side wall 5 which defines a substantially cylindrical chamber 6 of internal diameter $d_2$. The walls of the vessel are of stainless steel because it is relatively inexpensive and practical, though other metals such as gold, copper or brass, which reduce loss of microwave energy at the walls, could also be used.

A magnetron 7 is coupled to a tubular inlet 8 of the sidewall 5 through which the antenna 9 of the magnetron 7 extends into the interior of the chamber 6. The side wall inlet 8 is coupled by welding to the front, substantially planar, face 10 of the body 11 of the magnetron 7 forming a substantially microwave radiation leak proof seal between the vessel 2 and magnetron 7.

The magnetron 7 is coupled to the vessel 2 at a position off centre with respect to the inter-end wall separation distance $d_1$ such that the antenna 9, which extends substantially parallel to the end walls 3, 4 of the vessel, is at a distance $d_4=10.5$ cm from the first end wall 3 and $d_5=2.5$ cm from the second end wall 4 of the vessel 2. The distance $d_5$ can be readily determined experimentally such that the antenna 9 is positioned at approximately the mid point between a maximum point and a minimum point of the electric field of the standing wave along the length of the vessel. The magnetron 7 has a microwave output frequency of ca 2.45 GHz and power output of 1400 W and generates microwaves in the chamber of wavelength ($\lambda$)=approximately 13 cm. The microwave radiation is emitted from the antenna 9 into the chamber 6. The distal end 13 of the antenna 9 projects a distance $d_3$ from the sidewall 5 of the chamber 6. Each of the various more or less critical dimensions of the apparatus are related to the wavelength as follows: $d_1 \simeq \lambda$; $d_2 \simeq 1.3\lambda$; $d_3 \simeq \lambda/5$.

The vessel 2 has a pipeline 14 that extends into and through the chamber 6 of the vessel 2 from the first end wall 3 towards the second end wall 4 of the vessel 2. The pipeline 14 is substantially coaxial and concentric with the cylindrical chamber 6. The vessel end walls 3, 4 are formed of metal, such as copper or brass. The wall of the pipeline 15 is of PTFE (which is substantially transparent to microwave radiation). The microwave radiation enters the interior of the pipeline 16, through the pipeline wall 15. The pipeline 14 has an outer diameter $d_6 \geq \lambda/\pi$ (approximately 48 mm) and an inner diameter $d_8$ of approximately 30 mm.

Fluid 17 to be treated by the apparatus 1 flows through the pipeline 14, in the direction shown by the arrows, from the first end wall 3 of the vessel 2 towards the second end wall 4 of the vessel 2, and is subjected to microwave radiation as it passes through the interior of the pipeline 16 though the chamber 6.

The microwave radiation resonating in the vessel chamber results in varying input power levels of radiation being provided along the longitudinal axis of the pipeline between the first and second end walls of the vessel chamber. Substantially angularly uniform energy values can be obtained when the vessel chamber diameter $d_2$ to length $d_1$ ratio is in the range 1-2. Under such conditions and when the microwave radiation enters the vessel chamber at a preferred position along the length of the pipeline axis between the first and second end walls of the vessel chamber, the resonating microwave radiation has maximum intensity at one or more positions between the first end wall and second end wall of the vessel chamber (depending on how many $\lambda/2$ units $d_1$ corresponds to), and minimum microwave intensity at the vessel end walls (and between maxima where there are two or more).

For the apparatus of FIG. 1, the energy of the resonating microwave radiation increases progressively in generally sinusoidal manner along the central longitudinal axis of the pipeline 14 from a minimum value at the first end wall 3 of the vessel 2 to a maximum value at approximately 25% of the inter-end wall separation from the first end wall 3 of the vessel 2. The energy then decreases to zero before increasing to another maximum at 75% and finally decreasing again as the second end wall 4 of the vessel is approached to zero.

In general, it has been found that when $d_1$ is a multiple of $\lambda/2$ microwave radiation energy maxima may be found at positions equal to 25% and 75% of $d_1$ along the length of $d_1$ and energy minima at 0%, 50% and 100% of $d_1$ along its length, although the detailed energy distribution within the chamber is complex. Within the pipeline, the distribution is also dependent on the properties of the fluid therein. For example, where a fluid such as blood with a high level of electrical conductivity is flowing through the pipeline, microwaves can penetrate further inwards radially of the pipeline than when fluids such as tap water with a relatively low conductivity are being treated. The conductivity of the fluid being treated, therefore, is also a determining factor in the choice of the diameter of the pipeline.

Figure 2:
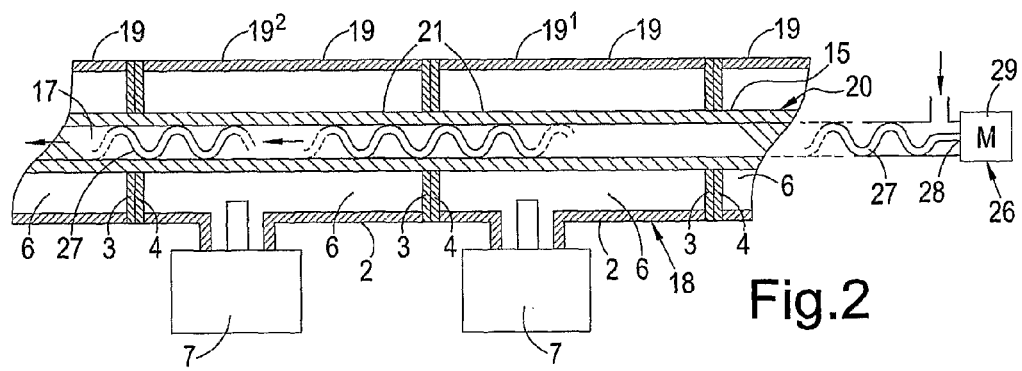
FIG. 2 is a schematic view of another multi-module, fluid treatment apparatus.

FIG. 2 shows a modular form of fluid treatment apparatus 18 in which a plurality of individual modules 19, similar to the apparatus shown in FIG. 1, are interconnected in series. The upstream end walls 3 of the vessels 2 of the modules 19 are coupled to the downstream end walls 4 of the vessels 2 of successive (downstream) modules 19. The vessel walls 3, 4 are releasably clamped to each other, conveniently by means of releasable fasteners such as nuts and bolts. The vessel walls 3, 4 are formed of copper or brass and are in the form of a diaphragm which minimises the propagation of microwave radiation between neighbouring modules 19, the diaphragm and the pipeline 20 being a relatively close contact fit with each other.

A single common pipeline 20 passes through the vessel 2 of the individual modules 19 to provide a pipeline segment 21 at each module 19. Fluid 17 flowing through the pipeline 20, in the direction shown by the arrows, sequentially enters successive modules 19 each of which is provided with a magnetron 7, as in FIG. 1. The magnetrons 7 of each module 19 provide microwave radiation to treat the fluid 17 present in the respective segment 21 of pipeline 20 of the module 19. The fluid 17 is subjected to successive microwave radiation treatments in the sequential modules 19 as it flows along the pipeline 20. The pipeline 20 is restricted to an outer diameter $d_6$ of the order of $\lambda/\pi$ so as to limit transmission of microwave radiation from the chamber 6 of one module $19^1$ to another $19^2$ and minimise interaction of the magnetrons 7 in the interconnected modules $19^1$, $19^2$.

A pump P and two valves 22 upstream of the vessel 2 control the rate of flow of the fluid through pipeline 14. A temperature sensor 23 is provided to read the temperature of the fluid being treated in the pipeline 14 of the vessel 2. A control unit 24 monitors temperature. The control unit 24 is connected 25 to the pump P and magnetron 7. The control unit 24 controls the rate at which the pump P pumps fluid through the pipeline 14 (and optionally the power output of the magnetron 7), according to the temperature of the flowing fluid 17 to ensure the fluid 17 is heated sufficiently to provide adequate treatment but prevent the fluid 17 overheating. In order to prevent build up of deposits from the fluid being treated on the pipeline wall 15, there is provided a flow rotation unit 26 comprising a generally rigid helical wire 27 drivingly connected 28 to a rotary drive 29 in the form of an electric motor M.

Figure 3:
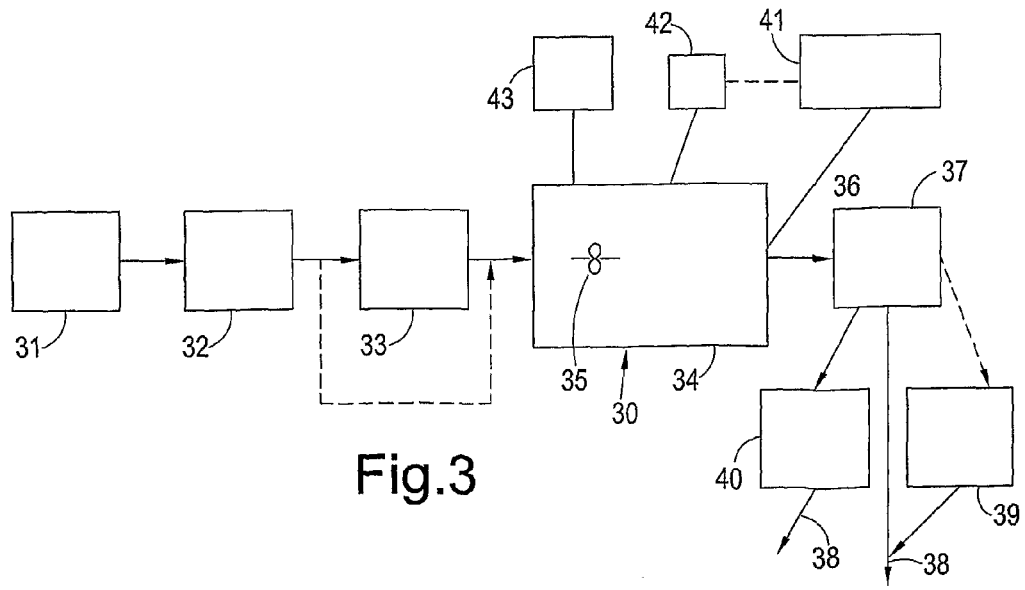
FIG. 3 is a schematic representation of a blood waste treatment system.

FIG. 3 shows a blood waste treatment system 30 comprising a storage vessel 31 for holding liquid blood waste, which is transferred therefrom by a pump 32. A pre-heater 33 is provided for heating the liquid blood waste up to around 35 to 37° C. in order to increase the efficiency of the microwave radiation treatment, whilst avoiding the risk of raising the temperature of the liquid blood waste to a level at which coagulation could occur. A microwave treatment apparatus 34 is provided. This has a number of individual modules, for example ten, (as described with reference to FIG. 1) connected in series (as shown in FIG. 2). The microwave treatment apparatus 34 includes a stirring device 35 in the form of a flow rotation unit, which is activated when fluid flows through the apparatus.

The device is generally similar to that shown in FIG. 2 but comprises two stainless steel helical wires, each having a diameter (of the wire itself) of approximately 4 mm, twisted together to form a more rigid and more effective stirrer. Operation of the flow rotation unit to rotate the fluid helps to prevent the pipeline becoming blocked and reduces the time required to clean the system. The temperature of the treated blood waste at the outlet 36 of the microwave treatment apparatus 34 will typically reach a temperature in the region of 80 to 100° C. As a result separation of the treated blood waste into sludge and concentrated liquid will generally take place. The liquid portion is introduced into a settling tank 37 and after a suitable settling period (typically 30 minutes), the liquid phase is discharged into the public sewer 38.

If a further sterilisation treatment is required, the liquid portion of the microwave treated blood waste could be passed to a further treatment apparatus 39, conveniently using a high-voltage pulse electrical discharge realised directly in the liquid such as that described in WO99/47230 the contents of which are incorporated herein by reference. The sludge can be utilised directly as organic fertiliser or first dewatered by centrifuge 40.

In order to maintain optimum operation, the system 30 includes a temperature sensor 41 to measure the temperature of the blood waste at the outlet 36 of the microwave treatment apparatus 34. A control unit 42 is also provided for monitoring and regulating blood waste flow rate that can optionally be connected to the temperature sensor so as to regulate the flow suitably so as to maintain the fluid outflow temperature at an appropriate level. An energy input unit 43 for controlling the microwave radiation source magnetrons of the microwave radiation apparatus 34.

Figure 4:
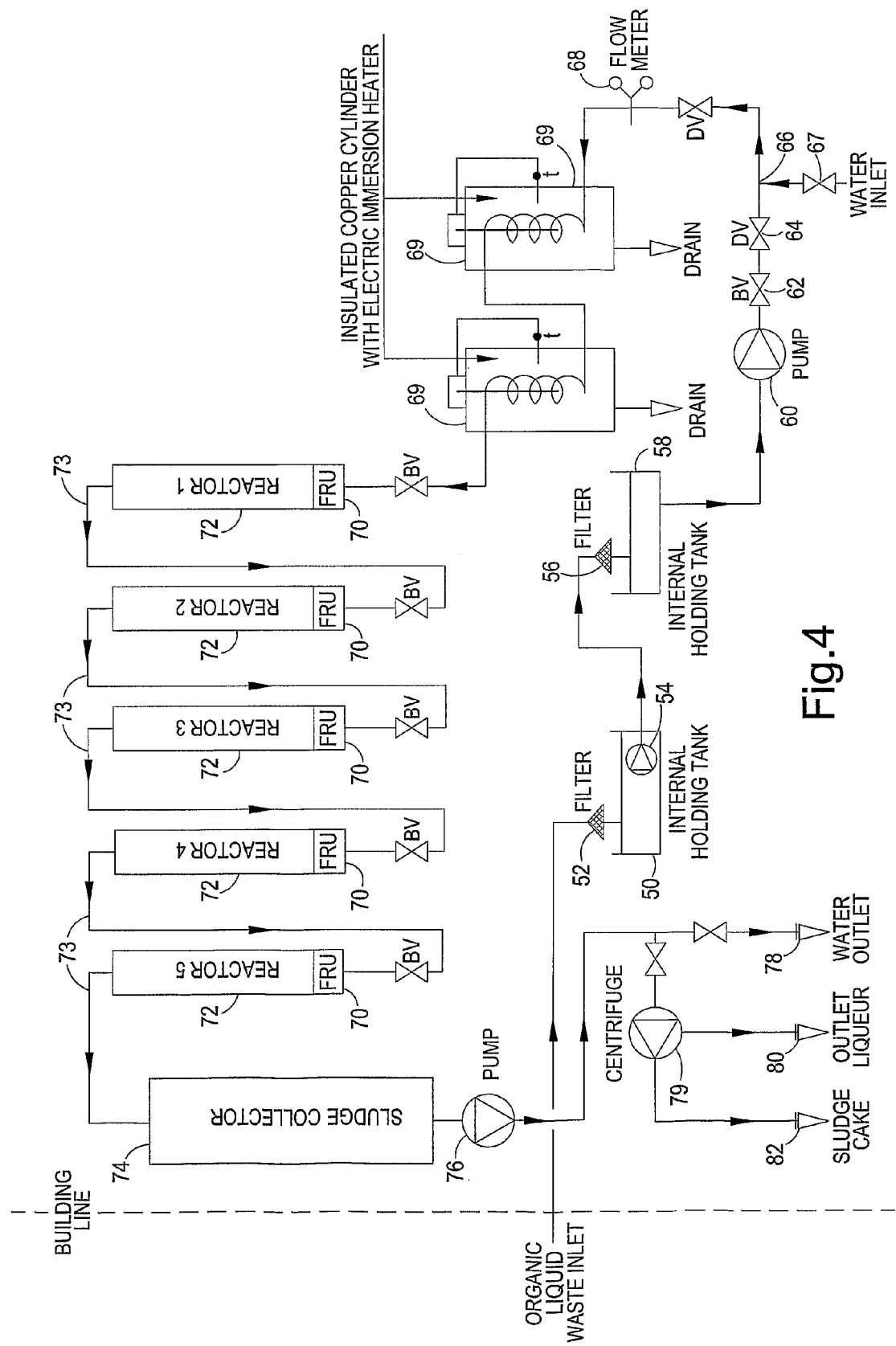
FIG. 4 is a more detailed representation of a blood waste treatment system.

FIG. 4 shows in more detailed view of a blood waste treatment system similar to that shown in FIG. 3. In this, arrowheads indicate the direction of fluid flow. Liquid waste to be treated is fed into a first storage vessel 50 through a coarse filter 52, consisting of a 8 mm mesh filter bag placed over a 3 mm mesh filter bag, from where it is pumped via pump 54 through a second filter 56 substantially similar to the first filter, into a second storage vessel 58. The liquid waste is pumped via a second pump 60 through ball valve 62 and diaphragm valves 64. The ball valve 62 is a simple and robust device but cannot readily provide an adjustable and precise flow rate of fluid, which is necessary to regulate the flow before the magnetron is switched on. The diaphragm valve 64 provides this adjustment.

When the apparatus is to be cleaned, water can be fed into the apparatus via a water inlet 66 under control of ball valve 67 and flushed through the pipes. The liquid waste to be treated passes through a flow meter 68, which monitors and controls the rate of flow of the fluid, and into two electrical preheaters 69, in series, from where it flows into a flow rotation unit, as described for FIG. 3, and into a first microwave radiation treatment reactor 72. Each reactor 72 comprises a series of ten modules connected as described for FIG. 2. The liquid waste flows via connecting pipes 73 to four further treatment reactors 72 connected in series and provided with respective flow rotation units 70. Following treatment, the treated liquid is collected in a settling tank 74 from where the liquid phase is pumped (via pump 76) via a water outlet 78 directly to the public sewer or into a centrifuge 79 for further separation of solid and liquid components. The liquid phase and solid phase are discharged via liquid phase outlet 80 and sludge cake outlet 82.

Blood from an abattoir was passed through an apparatus similar to that of FIG. 4 with 50 modules each having a chamber length $d_1$ and diameter $d_2$ of 13 cm and 17 cm, respectively, via a pipeline having an outer diameter $d_6$ of 48 mm and inner diameter $d_8$ of 30 mm, and each having a 1400 W magnetron microwave source providing microwave radiation with a wavelength of 12.24 cm inside the chamber. The blood was pumped through the apparatus at a flow rate of 2000 liters/hour thereby providing a residence time within each chamber of the apparatus of 15 seconds, and a total microwave irradiation treatment residence time of 12.5 minutes. The blood was preheated so that the temperature of the blood at the upstream end of the apparatus was 35 to 37° C., which increased to around 90° C. to 98° C. at the downstream end of the apparatus.

The benefits of the treatment of fresh blood waste produced by abattoirs was confirmed by measuring the proportion of solids and liquid resulting from the fractionation of blood by coagulation and by analysing the constituents of each fraction. It was found that virtually all of the protein contained in the blood remained in the solid fraction which represents 50-60% of the treated total, leaving a liquid (40-50%) consisting mostly of water with a greatly reduced Biological Oxygen Demand (BOD). The BOD of this liquid is sufficiently low to be simply treated in a conventional sewage system. The BOD of the blood was assesed using standard procedures, as described in "Standard Methods of Water and Waste Water Analysis" according to the American Public Health Association. Oxygen demand indexes BOD (biological oxygen demand) and COD (chemical oxygen demand) of the treated liquid are typically reduced by a factor of 20 to 25 when compared with the untreated blood. The actual extent of BOD and COD reduction achieved in any given case depends on the type of blood, its age and degree of its dilution etc. For example, when sheep blood waste was treated the BOD was reduced from 72,000 mg/ml to 4,000 mg/ml, and when chicken blood was treated the BOD was reduced from 23,000 mg/ml to 918 mg/ml.

As well as reducing the volume of material to be disposed of the concentrated high protein solids are sterile and free from any pathogens. This enables the solid material to be stored for long periods if aseptically filled into sterile containers. This stability enables these solids to be used as a high quality protein source else where in industry.

Figure 5:
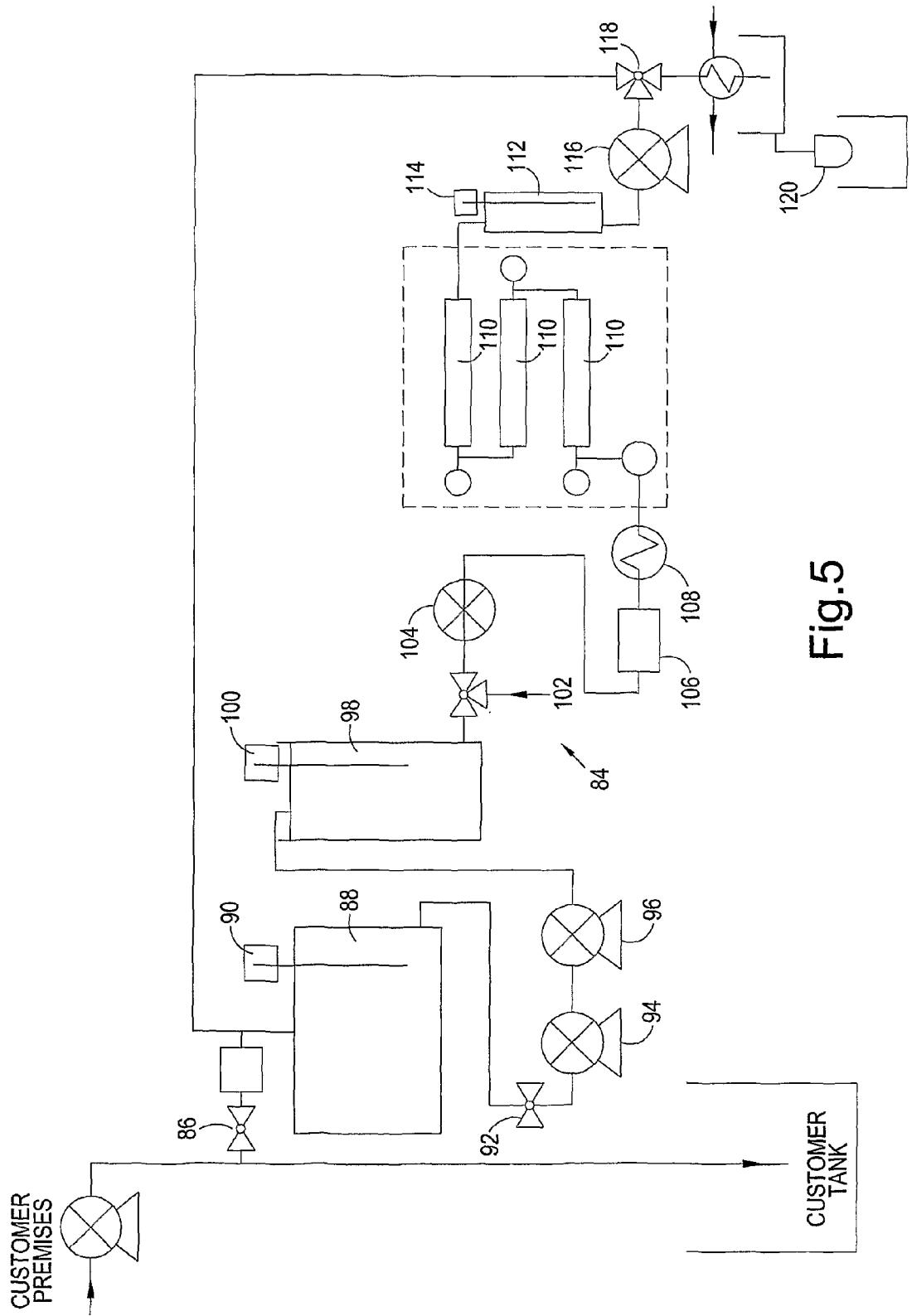
FIG. 5 is a schematic view of yet another multi-module, fluid treatment apparatus.

FIG. 5 shows an example of a waste treatment system 84 for use in an abattoir. This system is fully computerised with a PLC controlling all aspects of the process. In this example, the layout has an "on/off" valve 86 allowing the process access to raw blood, a raw material storage tank 88 with a level sensor 90, a valve 92 to switch the flow on or off, a macerator 94, a pump 96, a process holding tank 98 with level sensor 100, a two-way valve 102 including a connection point for a water purge 104, a flow meter 106 (flow control & volume recording), a heat exchange unit 108, three treatment chambers in accordance with the invention assembled horizontally in series 110, a sealed buffer tank 112 with level sensor 114, an auger fed positive displacement pump 116, a heat recovery unit, a two-way valve 118 to divert partially treated blood back to the holding tank 88 and a dewatering system 120.

Blood from the abattoir is fed into the raw material tank and pumped through the macerator 94 into the stainless steel process holding tank 98 on demand. The raw material and process holding tanks 88 and 98 are each installed with a level sensor 90 and 100, which provides high-high, high, low and low-low level indications. When the blood in holding tank reaches the high point/level the PLC system automatically switches off the macerator 94 and pump 96. The holding tank and an external water supply are connected to the treatment system via a two-way valve, and a pump. An electronic flow meter is provided at this stage to control/record the incoming volumes of blood.

During start up, water is introduced via the two-way valve into the treatment chambers 110. The magnetron water-cooling system is then switched on to cool down the magnetrons. When the flow meter indicates the presence of water in the system, the filaments of all the magnetrons in the treatment chambers 110 are switched on, and two minutes later the high voltage power supplies to all of the magnetrons are switched on sequentially. The water may be provided from the abattoir's main water supply or an independent tank with a separate pump and a non-return valve. The water is initially pumped through at a preset rate (in this instance 1200 L per hour). This ensures that the temperature of the water rises quickly yet avoids overheating. When the temperature of the water leaving the last treatment chamber reaches the desired temperature (65 degrees C.) the blood is switched on and the water switched of by the two-way valve. Blood is then pumped through the first heat exchange 108 where it is heated to around 39-40° C. before passing into the three treatment chambers 110. These are all on-line at any given time, although each can be by-passed to allow cleaning and removal of blockages without compromising the operation. The pressure and flow of the blood as well as the inlet and outlet temperature of each treatment chamber is monitored, by the PLC. This enables the PLC to control the final end product temperature at the desired level (95-100 degrees C.) by adjusting the pump speed.

The last chamber of the treatment unit is connected via a stainless steel pipe to a sealed thermo insulated buffer tank. This is connected via a pump to the second sealed water-cooled heat exchange unit where the temperature of the treated residue is reduced from 100° C. to ambient temperature. By using the temperature of the treated material, hot water can be returned back to the abattoir as a part of an energy saving scheme.

After cooling down to room temperature the treated thick liquid is fed to the dewatering system 120, which can be a simple tank with a filtered water outlet on the bottom or a dewatering screw or centrifuge if considered necessary, where the treated material is allowed to dry out. After the water is removed the solid "cake" can then be removed and sold.

If a sterile material is required the final buffer tank, pump and dewatering system is replaced by an aseptic hot fill line which enables the sterile treated material to be filled into aseptic containers to preserve shelf life.

An emergency/purge mode is provided in case any soft semi-solid organic material sticks to the walls of the treatment chambers and gradually builds up and restricts the flow. Early detection of such a scenario is achieved by the monitoring any increases in the process pressure. This system is designed to operate at up to 2 Barr pressure but generally operates at about 0.4 barr. Although uncommon a small pressure increase (0.2 barr) indicates a slight build up which is quickly removed by shutting off the blood and flushing with water for a few minutes. The treatment temperature is maintained by adjusting the flow rate of the water. This can be done using pump speed.

In practice, the most vulnerable component is the third treatment chamber 110. At this stage, the liquid is sticky and highly viscous with semi-solid inclusions. The semi-solid particles can stick to the inner walls of the treatment chamber and become centres for the build up of semi-solid formations. By changing the direction of the rotation device at the same time the water is introduced fast removal of any solid build up can be assisted.

The system of FIG. 5 is capable of producing a sterile material at an output temperature of at least 98 C at atmospheric pressure. Extensive cultivation of any product at a temperature of 98 C or higher (maximum tested 105 C) has failed to demonstrate any viable bacteria of any genera (either gram-positive or negative spore-forming) in material from abattoir blood output from the system of FIG. 5. Tests have been performed on *Escherichia coli* NCTC 10418, *Salmonella enterica* sv typhimurium NCTC 74 (ATCC 13311), *Salmonella enterica* sv seftenberg NCTC 9959, *Clostridium perfringens*. NCTC 3181 or equivalent and *Enterococcus faecalis* NCTC12697. Some of these bacteria are easily killed by thermal heating around 80-85 C. So in the case of gram-negative bacteria like *Salmonella enterica* and *Escherichia coli* NCTC 10418, it is difficult to separate microwave and thermal impacts. However, in the case of *Clostridium perfringens* NCTC 3181, total eradication by thermal means alone would require temperatures pressures and retention times greater than those described above. Hence, demonstrating that the present invention is more efficient at killing pathogens than conventional systems and can be used to pasteurise and sterilise liquids at much lower temperatures than would be required were heat alone used.

Microwave treatment of blood waste or other high protein liquids has significant advantages over traditional heat treatment methods using heat transfer surfaces. The transfer of microwave energy directly into the body of the liquid blood waste flowing through the pipeline makes it possible to avoid the particular problems associated with the inevitable substantial temperature differentials arising between the walls and/or heating element, and different parts of the liquid being treated. This differential leads to localised overheating resulting in blood coagulation and the deposition of solid films or coatings on the heated surfaces. Such deposits have extremely low thermal conductivity which substantially decreases heat transfer from the heat source to the liquid being heated, leading to dramatically reduced treatment efficiency and overheating of heating elements and their possible damage. In less extreme cases the temperature differential can cause localised burning of the liquid and create flavour changes.

The present invention is more energy efficient than known systems. In situations where full heat recovery is possible from the electrical components and this recovered heat can be used to preheat the incoming liquid between 85% and 90% of the electrical energy consumed can be delivered to a highly absorbent liquid like blood. The combination of heat, the intense electromagnetic fields and the Microwave radiation created within the individual treatment chambers has an effect on the molecular structures of the fluid constituents greater than heat alone. This manifests itself in a number of ways. The most notable evidence of this effect is the reduction in temperatures, pressures and retention times to achieve full sterilization, the shredding of proteins at much reduced temperatures and pressures and the increase in yields and reaction times of certain chemical reactions. Reducing the temperature and pressure required for sterilisation reduces potential damage and for some products allows preservation of the texture. For foodstuffs this can also allow the preservation of flavour, for example in liquid food products like milk, freshly squeezed orange juice, etc. Other advantages are that the entire apparatus occupies a small space and has very low start-up and shutdown times allowing low cost stand by operation.

A skilled person will appreciate that variations of the disclosed arrangements are possible without departing from the invention. Although the computer control system has been described as a PLC any suitable computer or processor based control system could be used. Accordingly the above description of specific embodiments is made by way of example only and not for the purposes of limitation. It will be clear to the skilled person that minor modifications may be made without significant changes to the operation described.

The invention claimed is:

1. An apparatus for treating a flow of fluid with microwave radiation, the apparatus comprising:
    a vessel having a side wall and opposed first and second end walls defining a substantially cylindrical chamber, the first end wall being disposed a predetermined distance $d_1$ from the second end wall;
    a pipeline for flowing fluid through, the pipeline passing through the first end wall towards the second end wall of the vessel, the chamber and the pipeline being substantially co-axial and the pipeline being substantially transparent to microwave radiation; and
    a microwave radiation source and a microwave radiation inlet in the side wall of the vessel, wherein the microwave radiation source has a magnetron set back from the vessel sidewall and an antenna that extends from the magnetron through the microwave radiation inlet and towards and into the vessel chamber for admitting microwave radiation of wavelength λ into the chamber, wherein the distance $d_1$ is substantially equal to an integral multiple of λ/2 so that the chamber is a microwave resonator, wherein the microwave radiation inlet is off-center with respect to a longitudinal extent of the chamber ($d_1$), and wherein a distal (free) end of the antenna is disposed at a predetermined projecting distance $d_3$ from the chamber sidewall of less than or equal to λ/4 and greater than or equal to 3λ/16.

2. An apparatus as claimed in claim 1, wherein $d_1$ is in the range of 1 to 3 times λ/2.

3. An apparatus as claimed in claim 2, wherein $d_1$ is 1 or 2 times λ/2.

4. An apparatus as claimed in claim 3, wherein $d_1$ is substantially equal to λ.

5. An apparatus as claimed in claim 1, wherein the cylindrical chamber comprises an internal diameter $d_2$ in the range of 0.6λ and 2λ.

6. An apparatus as claimed in claim 5 wherein $d_2$ is in the range of 1λ to 2λ.

7. An apparatus as claimed in claim 1, wherein the vessel chamber walls are made of or coated with an electrically conducting material.

8. An apparatus as claimed in claim 1 wherein the microwave source has an output that has a frequency in the range from 2.3 to 2.7 GHz.

9. An apparatus as claimed in claim 1 wherein when $d_1$ is approximately equal to λ, then the microwave radiation inlet position is selected from: 10 to 15%, 30 to 35%, 55 to 60%, or 75 to 80% of $d_1$ from the first end wall to the second end wall.

10. An apparatus as claimed in claim 1 further comprising ferrite components configured to act as a microwave non-return valve for preventing microwave energy being reflected into a microwave radiation source.

11. An apparatus as claimed in claim 1, wherein the pipeline is substantially horizontal.

12. An apparatus as claimed in claim 1, wherein the pipeline is substantially vertical.

13. An apparatus as claimed in claim 1, wherein the pipeline is inclined.

14. An apparatus as claimed in claim 1 comprising temperature sensing and monitoring devices for sensing a temperature of the fluid being treated.

15. An apparatus as claimed in claim 14 wherein the temperature sensor is connected to a microwave radiation source control to vary the intensity of microwave radiation provided as a function of the temperature sensed.

16. An apparatus as claimed in claim 1, wherein the pipeline wall has a thickness in the range from 3 to 10 mm.

17. An apparatus as claimed in claim 1 comprising a static or dynamic mixer or stirring device inside the pipeline.

18. An apparatus as claimed in claim 1 comprising a preheating device for heating a fluid before it enters the pipeline.

19. An apparatus as claimed in claim 1 comprising a pump for driving the fluid through the pipeline.

20. An apparatus as claimed in claim 1 comprising a plurality of modules connected in series or in parallel so that a fluid flow can be subjected to microwave irradiation from the respective microwave radiation sources of successive modules.

21. An apparatus as claimed in claim 1 wherein the pipeline outer diameter $d_6$ is $\geq \lambda/\pi$.

22. An apparatus as claimed in claim 1 comprising a pressure control system to allow pressure in the apparatus to be varied.

23. An apparatus as claimed in claim 1, wherein a thickness of an annular space between inside of the vessel chamber and outside of the pipeline is substantially equal to $\lambda/2$.

24. An apparatus as claimed in claim 1, wherein the pipeline wall has a thickness in the range from 5 to 8 mm.

25. A method of treating a fluid with microwave radiation comprising the steps of:
providing a fluid treatment apparatus, the apparatus comprising:
a vessel having a side wall and opposed first and second end walls defining a substantially cylindrical chamber, the first end wall being disposed a predetermined distance $d_1$ from the second end wall;
a pipeline for flowing fluid through, the pipeline passing through the first end wall towards the second end wall of the vessel, the chamber and the pipeline being substantially co-axial and the pipeline being substantially transparent to microwave radiation; and
a microwave radiation source and a microwave radiation inlet in the side wall of the vessel, wherein the microwave radiation source has a magnetron set back from the vessel sidewall and an antenna that extends from the magnetron through the microwave radiation inlet and towards and into the vessel chamber for admitting microwave radiation of wavelength $\lambda$ into the chamber, wherein the distance $d_1$ is substantially equal to an integral multiple of $\lambda/2$ so that the chamber is a microwave resonator, wherein the microwave radiation inlet is off-center with respect to a longitudinal extent of the chamber ($d_1$), and wherein a distal (free) end of the antenna is disposed at a predetermined projecting distance $d_3$ from the chamber sidewall of less than or equal to $\lambda/4$ and greater than or equal to $3\lambda/16$; and
passing a flow of said fluid through the pipeline of said apparatus whilst subjecting it to microwave radiation from the microwave radiation source of said apparatus.

* * * * *